United States Patent
Goutayer et al.

(10) Patent No.: US 9,993,398 B2
(45) Date of Patent: Jun. 12, 2018

(54) METHOD FOR FORMING A DISPERSION COMPRISING DROPS, AND ASSOCIATED APPARATUS

(71) Applicant: CAPSUM, Marseilles (FR)

(72) Inventors: Mathieu Goutayer, Saint Malo (FR); Yan Eric Pafumi, Gardanne (FR)

(73) Assignee: CAPSUM, Marseilles (FR)

( * ) Notice: Subject to any disclaimer, the term of this patent is extended or adjusted under 35 U.S.C. 154(b) by 157 days.

(21) Appl. No.: 15/028,731

(22) PCT Filed: Oct. 16, 2014

(86) PCT No.: PCT/EP2014/072176
§ 371 (c)(1),
(2) Date: Apr. 12, 2016

(87) PCT Pub. No.: WO2015/055748
PCT Pub. Date: Apr. 23, 2015

(65) Prior Publication Data
US 2016/0262990 A1 Sep. 15, 2016

(30) Foreign Application Priority Data

Oct. 17, 2013 (FR) ..................................... 13 60098

(51) Int. Cl.
*A61K 8/04* (2006.01)
*A61K 8/19* (2006.01)
(Continued)

(52) U.S. Cl.
CPC ................ *A61K 8/04* (2013.01); *A61K 8/042* (2013.01); *A61K 8/19* (2013.01); *A61K 8/31* (2013.01);
(Continued)

(58) Field of Classification Search
CPC . A61K 8/04; A61K 8/042; A61K 8/19; A61K 8/31; A61K 8/34; A61K 8/345;
(Continued)

(56) References Cited

U.S. PATENT DOCUMENTS 5,330,835 A * 7/1994 Kikuchi ................. A23F 5/243
264/4.4

FOREIGN PATENT DOCUMENTS

FR 2973371 A1 9/2012
WO 0196009 A2 12/2001
(Continued)

OTHER PUBLICATIONS

FR 1360098 Search Report dated Jun. 26, 2014.
International Search Report for PCT/EP2014/072176 dated Jan. 8, 2015.

*Primary Examiner* — Irina S Zemel
(74) *Attorney, Agent, or Firm* — Pearne & Gordon LLP

(57) ABSTRACT

This method comprises the following steps: flowing drops of a first phase, through a circulation duct, into a second phase that is substantially immiscible with the first phase, each drop comprising a core formed from the first phase and a shell formed from a layer of coacervate inserted between the first phase and the second phase; recovering a dispersion containing drops and the second phase in a container; injecting a solution for increasing the viscosity of the second phase in the circulation duct or at the outlet of the circulation duct, upstream from the container.

12 Claims, 4 Drawing Sheets

(51) Int. Cl.
| | |
|---|---|
| B01F 13/00 | (2006.01) |
| B01J 13/10 | (2006.01) |
| B01F 3/08 | (2006.01) |
| C11D 3/50 | (2006.01) |
| A61K 8/37 | (2006.01) |
| A61Q 13/00 | (2006.01) |
| A61Q 19/00 | (2006.01) |
| A61K 8/31 | (2006.01) |
| A61K 8/34 | (2006.01) |
| A61K 8/44 | (2006.01) |
| A61K 8/58 | (2006.01) |
| A61K 8/73 | (2006.01) |

(52) U.S. Cl.
CPC ............... *A61K 8/34* (2013.01); *A61K 8/345* (2013.01); *A61K 8/37* (2013.01); *A61K 8/44* (2013.01); *A61K 8/585* (2013.01); *A61K 8/73* (2013.01); *A61Q 13/00* (2013.01); *A61Q 19/00* (2013.01); *B01F 3/08* (2013.01); *B01F 3/0807* (2013.01); *B01F 3/0861* (2013.01); *B01F 13/0062* (2013.01); *B01J 13/10* (2013.01); *C11D 3/505* (2013.01)

(58) Field of Classification Search
CPC . A61K 8/37; A61K 8/44; A61K 8/585; A61K 8/73; A61Q 13/00; A61Q 19/00; B01F 13/0062; B01F 3/08; B01F 3/0807; B01F 3/0861; B01J 13/10; C11D 3/505
See application file for complete search history.

(56) References Cited

FOREIGN PATENT DOCUMENTS

| WO | WO-2008121342 A2 * | 10/2008 | ............ A61K 9/113 |
|---|---|---|---|
| WO | 2011051033 A2 | 5/2011 | |
| WO | 2012089820 A1 | 7/2012 | |

* cited by examiner

METHOD FOR FORMING A DISPERSION COMPRISING DROPS, AND ASSOCIATED APPARATUS

This is a National Stage application of PCT international application PCT/EP2014/072176, filed on Oct. 16, 2014 which claims the priority of French Patent Application No. 13 60098 entitled "METHOD FOR FORMING A DISPERSION COMPRISING DROPS, AND ASSOCIATED APPARATUS", filed Oct. 17, 2013, both of which are incorporated herein by reference in their entirety.

The present invention relates to a method for forming a dispersion comprising drops, comprising the following steps:
- flowing drops of a first phase, through a circulation duct, into a second phase that is substantially immiscible with the first phase, each drop comprising a core formed from the first phase and a shell formed from a layer of coacervate inserted between the first phase and the second phase;
- recovering a dispersion containing drops and second phase in a container.

This method is for example intended to form a dispersion of the oil-in-water type comprising disperse phase stable drops with a size larger than 500 microns, and in particular comprised between 500 microns and 2500 microns, preferably between 700 microns and 1500 microns.

The disperse phase is for example intended to contain a cosmetic product, a biologically active product, or an edible product able to be consumed.

Application WO 2012/120043 describes a manufacturing method of the aforementioned type. This method makes it possible to manufacture a stable dispersion of drops of a first phase into a second phase that is substantially immiscible with the first phase.

Each drop includes a core formed from a first phase and a very fine shell. The shell is formed from a very fine layer of coacervate, inserted between the first phase and the second phase to guarantee the stability of the drops.

To that end, in the method, a first fluid comprising a first phase and a first precursor polymer of the coacervate is injected in the form of drops into a second fluid intended to form the second phase.

A second precursor polymer of the coacervate is next brought into the second fluid and diffuses at the interface with the drops to form the coacervate layer.

Such a method is particularly effective to form drops with a perfectly controlled size, guaranteed stability, and having very satisfactory optical properties.

However, in the case of oil-in-water dispersions, the second aqueous phase must be fluid enough to allow good emulsification at the injection duct of the first phase into the second phase.

Under these conditions, when the dispersion obtained at the end of the method is recovered in a container, it has a second phase that is rarely suspensive, with a viscosity too low to give the product an agreeable texture.

Furthermore, when the anionic polymer forming part of the layer of coacervate is of the polyacrylic acid type (carbomer or derivative), the pH of the second phase is acid.

To offset this problem, the aforementioned application proposes adding a posteriori ingredients into the second phase, or replacing the second phase at least partially with another aqueous composition, in order to increase the viscosity of the second phase, or to gel it.

This operation is delicate, since the coacervate membrane surrounding the drops of oil is deformable and fragile. The manipulation of the obtained product, once the aqueous phase has gelled, is also delicate. In fact, the shearing at the water/oil interface caused by the flow, mixing, or withdrawal may cause a deformation and/or rupture of the oil drops, which deteriorates the visual properties of the product.

One aim of the invention is therefore to provide a simple method for obtaining a dispersion containing drops in a stable suspension in a phase, while minimizing the manipulations to be done on the product.

To that end, the invention relates to a method of the aforementioned type, characterized in that the method includes the following step:
- injecting a solution for increasing the viscosity of the second phase in the circulation duct or at the outlet of the circulation duct, upstream from the container.

The method according to the invention may comprise one or more of the following features, considered alone or according to any technically possible combination(s):
- the drops of the second phase flow along a local axis in the circulation duct, the injection of the solution increasing the viscosity being done substantially coaxially with the local axis;
- injecting of the solution increasing the viscosity includes bringing at least part of the solution increasing the viscosity to the center of the flow of the drops and the second phase;
- injecting of the solution increasing the viscosity includes bringing at least part of the solution increasing the viscosity to the periphery of the flow of the drops and the second phase;
- it includes reducing the cross-section of the flow of drops and the second phase, downstream from the injection of the solution increasing the viscosity;
- the solution increasing the viscosity is injected at the outlet of the circulation duct;
- it includes, upstream from the circulation step, a step for forming drops in the circulation duct;
- the step for forming drops comprises the following sub-steps:
  providing a first fluid comprising the first phase and a first precursor polymer of the coacervate contained in the first phase;
  forming drops of first fluid in a second fluid intended to form the second phase, the second fluid advantageously circulating in the circulation duct upstream from the injection of the solution increasing the viscosity;
  providing a second precursor polymer of the coacervate in the second fluid;
- it includes, during the injection step, the injection of a first solution increasing the viscosity, suitable for increasing the viscosity of the second phase,
- the method comprising, after the recovery step, the following steps:
  returning the intermediate dispersion, comprising a second phase with a partially increased viscosity, to circulation;
  injecting a second solution increasing the viscosity into the dispersion;
- the recirculation step includes the circulation of the dispersion in an additional duct, then the recovery of the dispersion in a container at the outlet of the additional duct, the injection of the second solution increasing the viscosity being done in the additional duct, or at the outlet of the additional duct, upstream from the container;
- the solution increasing the viscosity contains a base.

The invention also relates to an apparatus for forming a dispersion comprising drops, comprising:
- a circulation duct containing drops of a first phase in a second phase that is substantially immiscible with the first phase, each drop comprising a core formed from a first phase and a shell formed from a layer of coacervate inserted between the first phase and the second phase;
- a container for recovering a dispersion comprising drops and the second phase; characterized in that the apparatus includes:
- a reservoir containing a solution increasing the viscosity of the second phase;
- at least one injection duct of the solution for increasing the viscosity, connected to the reservoir, and emerging in the circulation duct or at the outlet of the circulation duct, upstream from the container.

The apparatus according to the invention may include one or more of the following features, considered alone or according to any technically possible combination(s):
- the circulation duct extends along the local circulation axis of the drops and the second phase, the injection duct emerging coaxially with the local axis;
- it includes a peripheral duct for injection of at least part of the solution for increasing the viscosity, emerging at the periphery of the circulation duct and/or a central injection duct for at least part of the solution for increasing the viscosity, emerging at the center of the circulation duct;
- it includes an assembly forming drops in the circulation duct, the drop forming assembly advantageously including:
  - a duct for providing a first fluid comprising the first phase and a precursor polymer of the coacervate contained in the first phase;
  - a duct forming drops of a first fluid in a second fluid intended to form the second phase, the second fluid containing or receiving a second precursor polymer of the coacervate.

The invention will be better understood upon reading the following description, provided solely as an example and done in reference to the appended drawings, in which:

FIGS. 1 to 3 illustrate the implementation of the first method for forming drops according to the invention.

Figure 1:
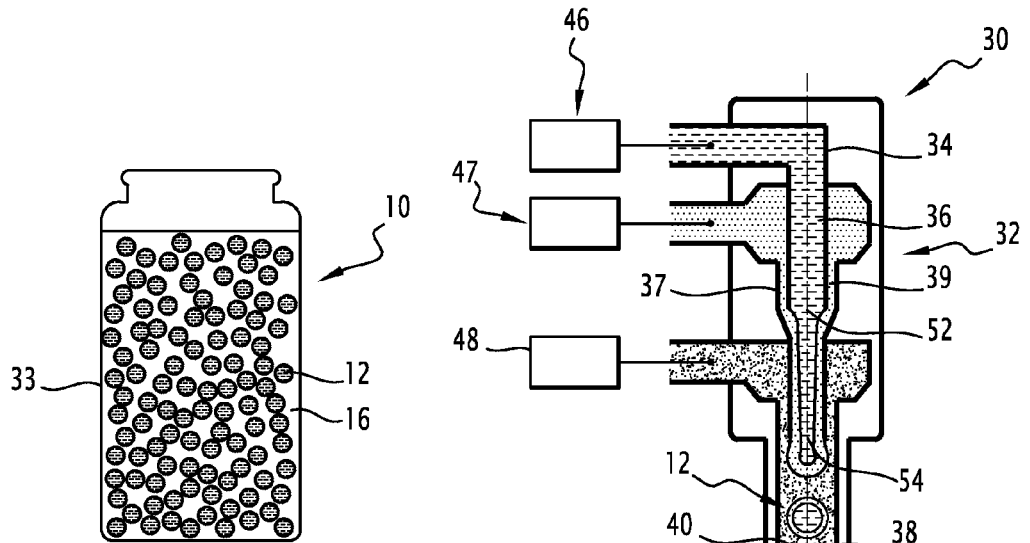
FIG. 1 is a side view of a container containing a dispersion obtained by a first method according to the invention.
Figure 2:
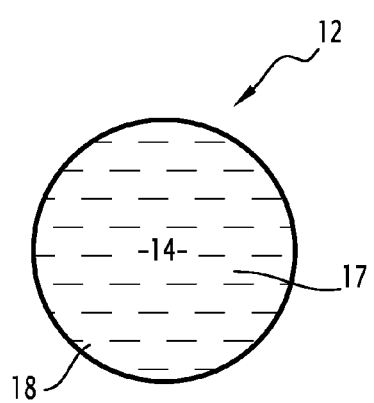
FIG. 2 is a sectional view of a drop of the dispersion according to the invention.

In reference to FIGS. 1 and 2, this first method is intended to form a dispersion 10 of drops 12 of a first phase 14 dispersed into a second phase 16. The second phase 16 is substantially immiscible with the first phase 14.

In this example, the first phase 14 or the disperse phase is an oily phase. It in particular contains, in liquid form, a first product that is chosen from among a biologically active product, a cosmetic product, or an edible product able to be consumed.

When the first product is a biologically active product, it is chosen from among anticoagulants, antithrombotics, antimitotic agents, antiproliferative agents, anti-adhesion agents, anti-migration agents, cell adhesion promoters, growth factors, antiparasitic molecules, anti-inflammatories, angiogenics, angiogenesis inhibitors, vitamins, hormones, proteins, antifungals, antimicrobial molecules, antiseptics or antibiotics.

Alternatively, the first phase 14 contains reactive agents such as proteins or reagents intended to form a bio-reagent, or to form artificial cells for implants.

A cosmetic product able to be contained in the core is for example cited in Directive 93/35/CEE by the Council dated Jun. 14, 1993. This product is for example a perfume, cream, emulsion, lotion, gel or oil for the skin (hands, face, feet, etc.), a makeup foundation (liquid, paste), a bath and shower preparation (salts, forms, oils, gels, etc.), a haircare product (hair dyes and bleaches), a cleaning product (lotions, powders, shampoos), a scalp maintenance product (lotions, creams, oils), a hairstyling product (lotions, hair sprays, brillantines), a shaving product (soaps, foams, lotions, etc.), a product intended to be applied on the lips, a sun product, a sunless tanning product, a product making it possible to bleach the skin, an anti-wrinkle product.

The edible products able to be consumed by a human or animal are advantageously purées of vegetables or fruits such as mango purée, pear purée, coconut purée, onion cream, leek cream, carrot cream, or other preparations that can mix several fruits or vegetables. Alternatively, it involves oils such as a dietary oil, such as olive oil, soy oil, grape seed oil, sunflower oil, or any other oil extracted from plants.

The second phase 16, or continuous phase, is advantageously aqueous. During the formation of the drops 12, the second phase 16 is for example made from an aqueous or hydraulic solution.

In one alternative, the second phase 16 comprises molecules of cosmetic interest, such as active ingredients, dyes, stabilizers, preservatives, modifying agents chosen from among texture, viscosity, pH, osmotic force or refractory index modifier agents.

Alternatively, the first phase 14 is an aqueous phase. The second phase 16 is then an oily phase.

The oil making up the oily phase is for example a silicone oil, mineral oil, plant oil, synthetic oil or a mixture of these oils.

Advantageously, the dispersion 10 is substantially translucent.

"Substantially translucent" means that the absorbance of the dispersion according to the invention is generally lower than 5%, preferably lower than 2%, preferably lower than 1% for at least one wavelength in the visible spectrum comprised from 400 nanometers to 1000 nanometers, advantageously over the entire wavelength of the visible spectrum from 400 nanometers to 1000 nanometers.

The intensity transmitted through the dispersion 10 according to the invention is divided by a factor of at least $10^3$ compared with a traditional concentrated emission.

This translucency is measured by introducing a dispersion scale into a basin with an optical thickness of 2 mm at a wavelength comprised between 400 nanometers and 1000 nanometers.

The first phase 14 and the second phase 16 are substantially immiscible. Thus, the solubility of the first phase 14 in the second phase 16 is advantageously less than 5% by mass.

The method according to the invention makes it possible to obtain a plurality of drops 12 of the first phase 14 as illustrated in FIG. 2.

Each drop 12 thus includes a core 17 made up of a first phase 14 and a shell 18 for retaining and stabilizing the core 17, the shell 18 being formed by a coacervate between a first precursor polymer and a second precursor polymer, as described in detail below.

In the example shown in FIG. 1, each drop 12 is suspended in the second phase 16 in which it is dispersed.

In the example shown in FIG. 1, the viscosity of the second phase 16 has been increased to keep the drops 12 in suspension.

Initially, during the formation of the drops 12, the viscosity of the second phase 16 is advantageously less than 20,000 mPa·s, preferably below 2500 mPa·s.

Once the drops 12 are formed, the viscosity of the second phase 16 is increased to be greater than 3000 mPa·s, preferably greater than 5000 mPa·s, or even to be totally gelled.

This viscosity also gives the dispersion 10 a pleasing texture to the touch.

The increase of the viscosity, or even its gelling, is obtained by injecting a solution for increasing the viscosity, according to the method that will be described below.

If the second phase 16 is an aqueous phase, the solution for increasing the viscosity is for example a solution containing a base, in particular an alkaline hydroxide, such as sodium hydroxide.

The viscosity is measured at ambient temperature, for example T=25° C.+/−2° C., and at ambient pressure, for example 1013 mbar, using the following method.

A viscosimeter of the Brookfield type is used, typically a digital Brookfield RVDV-E viscosimeter (torsion torque of the spring of 7187.0 dyne-cm), which is a viscosimeter rotating at an imposed speed provided with a spindle. A speed is imposed on the rotating spindle and the measurement of the torque exerted on the spindle makes it possible to determine the viscosity by knowing the geometry/shape parameters of the spindle used.

For example, a spindle is used with size No. 04 (Brookfield reference: RV4). The shear rate corresponding to the measurement of the viscosity is defined by the spindle used and the rotation speed thereof.

The viscosity measurement is done for 1 minute at ambient temperature (T=25° C.+/−2° C.). Approximately 150 g of solution is placed in a beaker with a volume of 250 ml, having a diameter of approximately 7 cm such that the height of the volume occupied by the 150 g of solution is sufficient to reach the gauge marked on the spindle. Next, the viscosimeter is started at a speed of 10 revolutions/min. and one waits for the value displayed on the screen to stabilize. This measurement yields the viscosity of the tested fluid, as mentioned in the context of this invention.

Alternatively, if the phase 16 is aqueous, the oily drops 12 may accumulate on the surface of the container 33 receiving the dispersion 10, if the viscosity of the second phase 16 is not modified.

In this case, the drops 12 are positioned bearing on one another. Subsequently, the dispersion comprises at least one concentrated region including drops 12 and at least one region without drops 12 and exclusively comprising the second phase 16.

In the example shown in FIGS. 1 and 2, the diameter of the drops 12 is greater than 500 µm, and is advantageously less than 3000 µm.

Advantageously, the diameter of the drops 12 is comprised between 500 microns and 2500 microns. The drops 12 are visible in the aqueous phase 16.

In one embodiment, when the drops 12 of the dispersion 10 have a size greater than 500 µm, the drops 12 advantageously have a uniform size distribution.

More specifically, according to this embodiment, the disperse phase is made up of a population of monodisperse drops 12 such that they have an average diameter $\overline{D}$ comprised from 500 µm to 3000 µm and a variation coefficient Cv of less than 10%.

In the context of the present description, "monodisperse drops" refers to the fact that the population of drops of the dispersion according to the invention has a uniform size distribution. Monodisperse drops have a good monodispersity. Conversely, drops having a poor monodispersity are called "polydisperse".

The mean diameter $\overline{D}$ of the drops is for example measured by analyzing a photograph of a lot made up of N drops, using image processing software (Image J). Typically, according to this method, the diameter is measured in pixels, then converted to µm, based on the size of the container containing the drops 12 of the dispersion.

Preferably, the value of N is chosen to be greater than or equal to 30, such that this analysis provides a statistically significant reflection of the diameter distribution of the drops of said emulsion.

The diameter Di of each drop is measured, then the mean diameter $\overline{D}$ is obtained by calculating the arithmetic mean of these values:

$$\overline{D} = \frac{1}{N}\sum_{i=1}^{N} D_i$$

From these values $D_i$, it is also possible to obtain the standard deviation σ of the diameters of the drops in the dispersion:

$$\sigma = \sqrt{\frac{\sum_{i=1}^{N}(D_i - \overline{D})^2}{N}}$$

The standard deviation σ of a dispersion reflects the distribution of diameters $D_i$ of the drops of the dispersion around the mean diameter $\overline{D}$.

By knowing the mean diameter $\overline{D}$ and the standard deviation σ of the dispersion, it is possible to determine that 95.4% of the population of drops is found in the interval of diameters [$\overline{D}$−2σ; $\overline{D}$+2σ] and 68.2% of the population is found in the interval [$\overline{D}$−σ; $\overline{D}$+σ].

In order to characterize the monodispersity of the dispersion according to this embodiment of the invention, it is possible to calculate the variation coefficient:

$$C_v = \frac{\sigma}{\overline{D}}$$

This parameter reflects the distribution of the diameters of the drops as a function of the mean diameter thereof.

The variation coefficient Cv of the diameters of the drops of the dispersion 10 according to this embodiment of the invention is less than 10%, preferably less than 5%.

Alternatively, the monodispersity can be shown by placing a dispersion sample 10 in a vial with a constant circular section. Gentle agitation by rotating a quarter revolution over a half-second around the axis of symmetry crossing through the file, followed by rest for one half-second, is done, before repeating the operation in the opposite direction, four times in a row.

The drops 12 of the dispersion are organized in a crystalline form when they are monodisperse. Thus, they have a stack following a pattern repeating in all three dimensions. It is then possible to observe a regular stack that indicates a good monodispersity, an irregular stack reflecting polydispersity of the dispersion.

When the dispersion is left to rest, the drops 12 are stable and do not adhere to one another; no coalescence is observed after 2 weeks at 40° C.

The dispersion 10 according to the invention supports agitation without shearing without undergoing significant coalescence of the drops 12, or an alteration of its monodispersity.

To test this property, a sample of the dispersion 10 according to the invention is placed in a 2 mL container, then the latter is placed in a cell of an agitation plate (IKA vortex Genius 3). The size of a cell is approximately 50% larger than that of the container containing the sample. Thus, during agitation, the container collides with the walls of the cell, which creates a large number of impacts. The agitation speed is approximately 500 rpm. The test is considered successful when fewer than 5% of the drops by number have undergone coalescence at the end of one hour of agitation without shearing.

In addition to the properties stated above, such drops 12 are non-elastic, and have a granular behavior when the dispersion is agitated, such that they flow over one another like solid objects and adopt a particular behavior in suspension.

Furthermore, the dispersion 10 according to the invention can have the following properties.

According to certain advantageous embodiments, the dispersion 10 according to the invention supports a fall from a height of one meter without experiencing significant coalescence of the drops 12, or an alteration of its monodispersity.

To test this property, a sample of the dispersion 10 according to the invention is placed in a 2 mL container, then the latter is dropped from the top of a glass tube measuring one meter tall serving as a guide, on a solid substrate, and recovered at its lower end. The operation is repeated three times. The test is considered successful when fewer than 5% of drops 12 by number have undergone coalescence at the end of three falls.

The drops 12 are substantially non-elastic. The non-elasticity of the drops can be characterized by a very low flow resistance threshold, for example measured using the following method: a dispersion sample 10 is placed in a rheometer of the RFSII rheometrics type using a cone-plane geometry having an air gap of 45 micrometers. The studied shears were low, and in particular are comprised between $1\ s^{-1}$ and $10\ s^{-1}$. The sheer modulus is measured for increasing shears between $1\ s^{-1}$ and $10\ s^{-1}$.

Thus, the shear modulus, under low shearing, in particular equal to $2\ s^{-1}$, is less than 200 Pa·s, and is in particular less than 100 Pa·s.

This shear modulus is lower by at least 100 than the shear modulus observed at the same shearing, for a traditional dispersion stabilized by surfactants and having the same oil and water composition.

Compared with a traditional monodisperse emulsion (oil/water) concentrated at 80% (cf. Mason at al. J. Coll. Int. Sci. 179, 439-448 (1996)), an emulsion concentrated according to this embodiment has a viscosity η (Pa·s) lower by a factor of 100, for shearing from $1\ s^{-1}$ to $12\ s^{-1}$.

The core 17, even surrounded by the shell 18, is substantially liquid or not very gelled. Alternatively, the core is gelled.

Owing to the method according to the invention, the drops 12 obtained using this method have a very fine shell 18, in particular with a thickness of less than 1% of the diameter of the drops 12.

The thickness of the shell 18 is thus less than 1 μm and is too small to be measured using optical methods. This size is generally comprised between 1 nm and 500 nm, preferably smaller than 100 nm, advantageously less than 50 nm, preferably less than 10 nm.

The thickness of the shell of the drops 12 according to the invention can be measured using the small-angle X-ray scattering method, as implemented in Sato et al. J. Chem. Phys. 111, 1393-1401 (2007).

To that end, the drops 12 are produced by using deuterated water, then are washed three times with a deuterated oil, for example a deuterated oil of the hydrocarbonated type (octane, dodecane, hexadecane).

After washing, the drops 12 are next transferred into the neutron cell in order to determine the spectrum I(q); q being the wave vector.

From this spectrum, the traditional analytical treatment (REF) is applied in order to determine the thickness of the hydrogenated shell (non-deuterated).

The shell 18 surrounding the drops 12 of the dispersion according to the invention is stiffened, which imparts greater strength to the drops 12 and decreases, or even prevents, their coalescence.

This shell 18 is typically formed by coacervation, i.e., by precipitation of polymers charged with opposing charges. Within a coacervate, the bonds binding the charged polymers to one another are of the ionic type, and are generally stronger than bonds of the electrostatic type present within a membrane of the surfactant type.

The shell 18 is formed by coacervation of at least two polymers charged with opposite polarities (or polyelectrolyte), and preferably in the presence of a first polymer, of the cationic type, and a second polymer, different from the first polymer, of the anionic type.

In the context of the present description, "polymer of the anionic type" refers to a polymer including chemical functions of the anionic type. This may also be called anionic polyelectrolyte.

"Chemical function of the anionic type" refers to an AH chemical function capable of ceding a proton to give an $A^-$ function. Depending on the conditions of the medium in which it is found, the anionic-type polymer therefore has chemical functions in AH form, or in the form of its conjugated base $A^-$.

Examples of anionic chemical functions include carboxylic acid —COOH functions, optionally present in the form of carboxylate anion —COO—.

Examples of anionic polymers include any polymer formed by the polymerization of monomers whereof at least part bears chemical functions of the anionic type, such as carboxylic acid functions. Such monomers are for example acrylic acid, maleic acid, or any ethylenically unsaturated monomer including at least one carboxylic acid function.

Examples of anionic-type polymers appropriate for carrying out the invention include copolymers of acrylic acid or maleic acid and other monomers, such as acrylamide, alkyl acrylate, C5-C8 acrylate, C10-C30 alkyl acrylate, C12-C22 alkyl methacrylate, methoxypolyethyleneglycol methacrylate, hydroxyester acrylate, cross-polymer acrylate.

In the context of the present description, "polymer of the cationic type" refers to a polymer including chemical functions of the cationic type. This may also be called cationic polyelectrolyte.

"Chemical function of the cationic type" refers to a B chemical function capable of capturing a proton to give a $BH^+$ function. Depending on the conditions of the medium in which it is found, the cationic-type polymer therefore has chemical functions in B form, or in the form of $BH^+$, its conjugated acid.

Examples of cationic chemical functions include primary, secondary and tertiary amine functions, optionally present in the form of ammonium cations.

Examples of cationic-type polymers include any polymer formed by the polymerization of monomers, at least part of which bears chemical functions of the cationic type, such as primary, secondary or tertiary amine functions.

Such monomers are for example aziridine, or any ethylenically unsaturated monomer including at least one primary, secondary or tertiary amine function.

Examples of cationic-type polymers appropriate for carrying out the invention include amodimethicone, derived from a silicone polymer (polydimethylsiloxane, also called dimethicone), modified by primary amine and secondary amine functions:

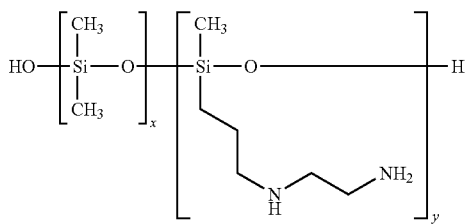

Amodimethicone

Examples also include derivatives of amodimethicone, for example copolymers of amodimethicone, aminopropyl dimethicone, and more generally silicone polymers including amine functions.

Examples include the copolymer of bis-isobutyl PEG-14/amodimethicone, Bis (C13-15 Alkoxy) PG-Amodimethicone, Bis-Cetearyl Amodimethicone and bis-hydroxy/methoxy amodimethicone.

Examples also include polymers of the polysaccharide type comprising amine functions, such as chitosan or derivatives of guar gum (guar hydroxypropyltrimonium chloride).

Examples also include polymers of the polypeptide type comprising amine functions, such as polylysine.

Examples also include polymers of the polyethyleneimine type comprising amine functions, such as linear or branched polyethyleneimine.

The coacervation generally takes place in the presence of a first polymer of the anionic type and a second polymer of the cationic type, which act as stiffening agents for the membrane.

The formation of the coacervate between these two polymers is generally caused by modification of the conditions of the reaction medium (temperature, pH, reagent concentration, etc.). The coacervation reaction results from the neutralization of these two polymers charged with opposite polarities and allows the formation of a membrane structure by electrostatic interactions between the first and second polymers. The membrane thus formed around each drop 12 forms a shell 18 that completely encapsulates the core 17 and isolates the first phase 14 from the second phase 16.

As will be seen later in the description of the method according to the invention, the first polymer is initially contained in one of the first phase 14 and the second phase 16, the second polymer initially being contained, before the formation of the drops 12, in the other of the first phase 14 and the second phase 16. The two polymers next migrate to the interface during the formation of drops, where they form the shell 18 by coacervation.

One advantageous dispersion is such that each drop 12 comprises, by mass relative to the mass of said drop:
 0.05% to 10% of a polymer P1 of the anionic and hydrophilic type, and
 0.05% to 10% of a polymer P2 of the cationic and lipophilic type.

Preferably, each drop 12 comprises, by mass relative to the mass of said drop, from 0.1% to 5% of a polymer P1 of the anionic and hydrophilic type.

Preferably, each drop 12 comprises, by mass relative to the mass of said drop, from 0.1% 5% of a polymer P2 of the cationic and lipophilic type.

One advantageous dispersion according to this alternative is such that each drop comprises an anionic and hydrophilic polymer P1, and a cationic and lipophilic polymer P2, in a weight ratio P1:P2 comprised between 1:10 and 10:1.

Figure 3:
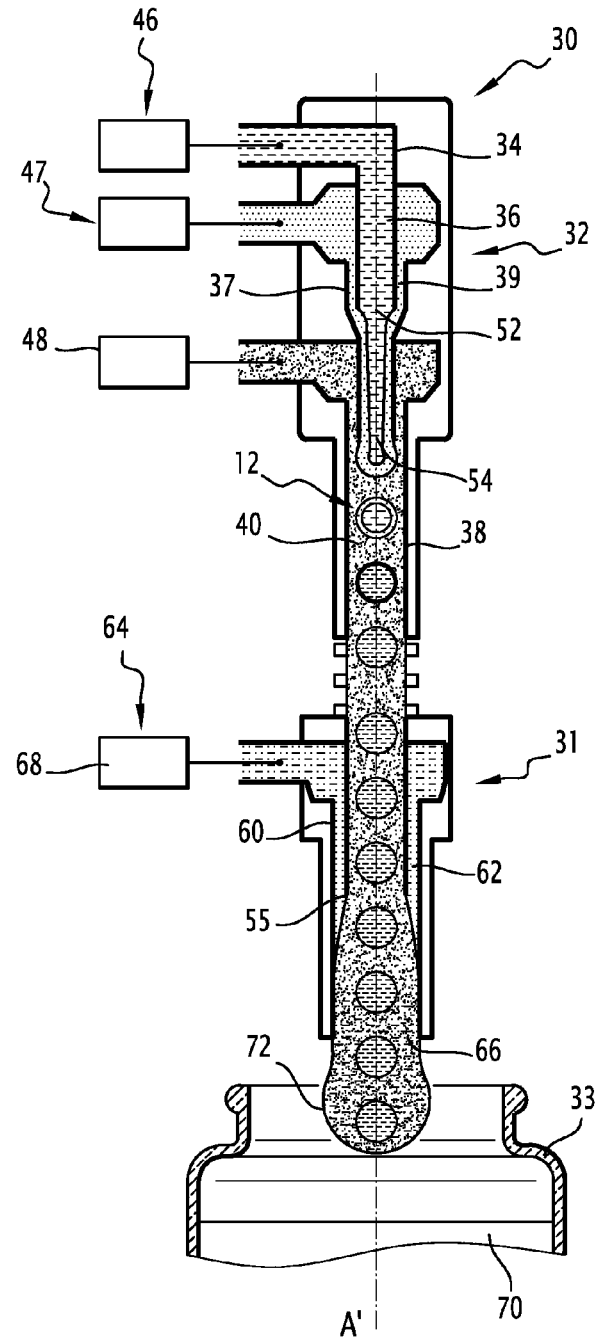
FIG. 3 is a diagrammatic partial sectional view of a first apparatus for manufacturing the dispersion, for carrying out the first method.

The first method according to the invention is carried out using a microfluidic method, in an apparatus 30 illustrated by FIG. 3.

This apparatus 30 includes a nozzle 32 for forming drops 12, a stage 31 for increasing the viscosity of the drops 12 and a receptacle 33 for receiving the formed drops 12.

The forming nozzle 32 includes an inner intake duct 34 bringing in an inner fluid 36 comprising the first phase 14, and advantageously, an intermediate intake duct 37 bringing in an intermediate fluid 39 intended to form a temporary screen.

The forming nozzle 32 further includes an outer circulation duct 38, positioned around the inner duct 34 and/or the intermediate duct 37 to bring and circulate an outer fluid 40 forming at least part of the second phase 16.

The apparatus 30 additionally includes intake means 46 for bringing an inner fluid 36 into the inner duct 34, intake means 47 for bringing an intermediate fluid 39 into the intermediate duct 37, and intake means 48 for bringing an outer fluid 40 into the annular space defined between the inner duct 34 and the outer duct 38.

In the example shown in FIG. 3, the maximum diameter of the duct 34, 37 and 38 is less than 3 mm in order to preserve the microfluidic nature of the method.

The inner duct 34 is advantageously positioned coaxially in the outer duct 38. It is connected upstream to the intake means 46. It emerges downstream through a downstream opening 52 positioned in the outer duct 38, withdrawn relative to the downstream opening 54 defined by the intermediate duct 37, above that opening 54.

Thus, the distance separating the downstream opening 52 of the inner duct 34 and the downstream opening 54 of the intermediate duct 37 is preferably greater than 1 time the diameter of the intermediate duct 37.

The intermediate duct 37 extends around the inner duct 34. It defines, with the inner duct 34, an annular space connected upstream to the intake means 47. The intermediate duct 37 emerges through the downstream opening 54.

The outer duct 38 defines, with the intermediate duct 37 and/or the inner duct 34, an annular space connected upstream to the intake means 48.

The outer duct 38 has a downstream opening 55 that is situated above and away from the container 33. It emerges in the stage for increasing the viscosity 31.

The intake means 46, 47 and 48 each for example include a syringe plunger, a peristaltic pump or another system generating pressure controlling the flow rate, for example a pressure pot coupled to a flowmeter and a flowrate regulating system.

Each of the intake means 46, 47 and 48 is able to convey a respective fluid 36, 39, 40 at a controlled and adjustable flow rate.

According to the invention, the stage 31 includes at least one duct 60 for injecting a solution 62 for increasing the viscosity, and intake means 64 for bringing the solution 62 into the duct 60.

In the example shown in FIG. 3, the stage 31 includes a peripheral duct 60 for injecting at least part of the solution for increasing the viscosity 62.

The peripheral duct 60 extends at the periphery of the outer circulation duct 38, coaxially with the local axis of the outer duct 38. The downstream opening 55 of the outer duct 38 extends in the peripheral duct 60.

The peripheral duct 60 defines, downstream from the downstream opening 55, a distribution opening 66 that emerges in the container 33 or above it.

The peripheral duct 60 defines, with the outer duct 38, an annular space that emerges upstream from the distribution opening 66 in the example shown in FIG. 3.

Thus, the peripheral duct 60 is configured to allow the injection of the solution for increasing the viscosity 62 coaxially with the circulation axis of the dispersion containing the drops 12 and the second phase 16, just at the outlet of the outer circulation duct 38.

In this example, the peripheral duct 60 is able to collect the drops 12 and the second phase 16 in which the solution 62 for increasing the viscosity has been introduced, and to convey them to the distribution opening 66.

The intake means 64 include a reservoir 68 containing the solution for increasing the viscosity 62, and a conveying unit (not shown).

The conveying unit for example includes a syringe plunger, a peristaltic pump or another system generating pressure controlling the flow rate, for example a pressure pot coupled to a flowmeter and a flowrate regulating system.

The container 33 is positioned below the distribution opening 66.

Alternatively, it contains a volume 70 of liquid intended to form part of the second phase 16, advantageously an external fluid volume 40.

The upper surface of the fluid volume 70 is situated axially away from the distribution opening 66, considered along the axis A-A' of the duct 60, such that the drops 12 that are dispersed in the second phase 14 fall under the effect of their weight through an air volume between the distribution opening 66 and the upper surface of the liquid volume 70.

In one alternative (not shown), the downstream opening 54 is submerged in the volume of liquid 70.

In the example shown in FIG. 3, the device 30 has been illustrated with a single nozzle 32, associated with a single stage 31 for increasing the viscosity.

Figure 6:
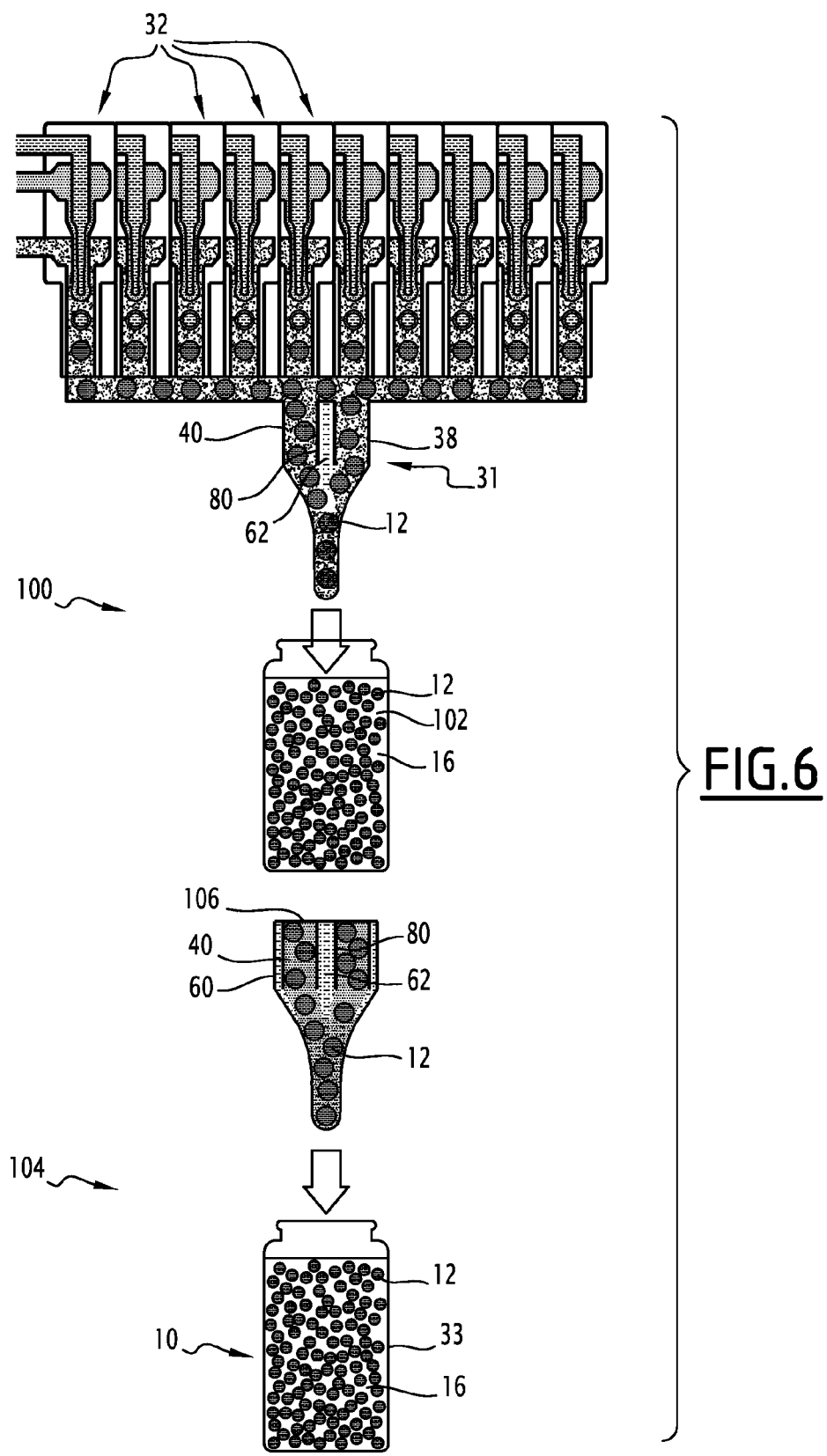
FIG. 6 is a view similar to FIG. 3 of an alternative apparatus for manufacturing a dispersion, for implementing a second method according to the invention.

In one advantageous alternative, illustrated at the top of FIG. 6, the system 30 includes a plurality of nozzles 32, all connected downstream from a shared stage 31 for increasing the viscosity, the nozzles 32 being positioned in parallel above a container 33. The nozzles 32 are laterally offset relative to the stage 31 for increasing the viscosity. A collection circuit makes it possible to collect the drops 12 in the liquid 40 at the outlet of each nozzle 32 to gather them and introduce them into the stage 31.

A first method according to the invention, implemented in the installation of FIG. 3, will now be described.

Initially, the inner fluid 36 is prepared by mixing the first phase 14 intended to form the core 17 of the drop 12 and a first precursor polymer of the coacervation.

In this example, the inner fluid 36 is advantageously oily. The first phase 14 contains at least one oil, and one compound to be dispersed, such as a perfume. The precursor polymer is lipophilic, and advantageously cationic.

The intermediate fluid 39 is also prepared. This intermediate fluid 39 is advantageously oily. It is for example paired with a base of the same oil as that contained in the first phase 14.

The outer fluid 38 is also formed. In this example, the outer fluid 38 is aqueous. It contains a second precursor polymer of the coacervation, here a hydrosoluble polymer, for example of the anionic type.

Advantageously, active ingredients, dyes, stabilizers, preservatives, modifying agents chosen from among texture, viscosity, pH, osmotic force and/or refractory index modifier agents are added in the outer fluid 38.

A solution for increasing the viscosity 62 is also prepared. This solution is advantageously aqueous. It includes a base, in particular an alkali hydroxide, such as sodium hydroxide.

Then, the inner fluid 36, the intermediate fluid 37 and the outer fluid 40 are respectively positioned in the respective intake means 46, 47 and 48.

The solution for increasing the viscosity 62 is arranged in the intake means 64.

A liquid 70, formed from an aqueous solvent similar in nature to the external fluid 40, is optionally introduced into the container 33.

Next, the intake means 46, 47, 48 and 64 are activated.

The inner fluid flow 36 circulating in the inner duct 34 coaxially enters the intermediate duct 37 at the downstream opening 52 of the inner duct 34.

The inner fluid 36 is then surrounded by the intermediate fluid 39 in the intermediate duct 37.

At the downstream opening 54 of the intermediate duct 37, drops 12 of inner fluid 36, surrounded by a film of intermediate fluid 39, form in the outer fluid 40.

The drops 12 then circulate in the outer fluid 40 toward the downstream opening 55.

The first polymer present in the inner fluid 36 migrates to the interface between the drops 12 and the outer fluid 40, by gradual diffusion in the intermediate fluid film 39.

Likewise, the second polymer present in the outer fluid 40 migrates to the interface between the outer fluid 40 and each drop 12.

The coacervation between the first polymer and the second polymer occurs to form the shell 18.

The first polymer and the second polymer not initially being present in the same phase, and a film of intermediate fluid 39 with no precursor polymers initially being present at the surface of the drops 12, the risk of them reacting prematurely, in particular before the formation of the drops 12 of inner fluid 36 in the outer fluid 40, is very limited. This guarantees that the shell 18 formed at the interface between the inner phase 14 and the outer phase 16 is complete, very thin, and does not cause total gelling of the core 17.

The drops 12 thus formed are therefore very stable, have little to no elasticity and do not tend to coalesce on one another.

The drops 12 stabilized in the outer fluid 40 then arrive at the stage 31 for increasing the viscosity.

The solution for increasing the viscosity 62 is then injected coaxially into the flow of drops 12 in the outer fluid 40, at the periphery of the outer fluid 40. The solution 62 diffuses in the outer fluid 40 during its transport through the downstream part of the peripheral duct 60.

The viscosity of the outer fluid 40 then increases significantly, to reach a value greater than 3000 mPa·s, preferably greater than 5000 mPa·s. Advantageously, the outer fluid 40 is gelled.

Likewise, the pH of the outer fluid 40 is neutralized.

The increase of the viscosity and the potential neutralization occur near the distribution opening 66, just before the introduction of the dispersion 10 into the container 33.

At least one drop 12 is next received in an outer drop 72 of outer fluid 40 that is formed at the outlet of the peripheral duct 60, at the distribution opening 66.

The outer drop 72 falls into the container 33 through a volume of air and the drops 12 of the first phase 14 remain suspended in the second phase 16 formed by the outer fluid 40 and by the liquid 70 when such a liquid is present in the container 33.

In one alternative, the outer fluid 40 forms a jet at the outlet of the peripheral duct 60 and is collected without fragmenting. Preferably, the jet becomes thinner between the outlet of the peripheral duct 60 and the container 33, in order to reduce the diffusion time of the agent for increasing the viscosity.

The neutralization and the increase in the viscosity of the second phase 16 are therefore conducted in a manner that is not very invasive, and directly in line with the manufacturing of the drops 12.

This guarantees the use of a fluid enough aqueous phase to authorize an appropriate formation of drops 12 at the nozzle 30. Nevertheless, the final product may comprise a satisfactory viscosity to give it a pleasant texture, without harming the stability of the formed drops 12, and at a lower cost.

The method according to the invention is therefore particularly effective to form stable drops 12, with dimensions larger than 500 µm, in a stable suspension in a phase 16, without the use of surfactants and in a particularly controlled manner.

The method according to the invention limits shearing, since the continuous second phase 16 containing the drops 12 remains fluid until the last moment. No force is created to deform or fragment the drops 12 when the viscosity of the continuous phase is increased.

Creaming is also reduced. The diffusion time of the solution 62 for increasing the viscosity in the continuous phase 16 is very low, in light of the small thickness to be crossed. The continuous phase 16 almost immediately acquires a suspensive nature when it is collected in the container 33.

Figure 4:
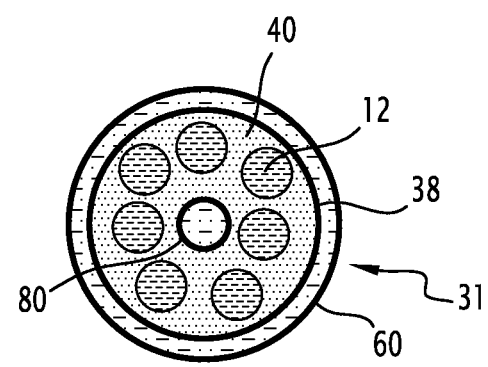
FIG. 4 is a detailed view of the end of a circulation duct of one alternative apparatus according to the invention, where the injection of a solution for increasing the viscosity is done at the end of the circulation duct.
Figure 5:
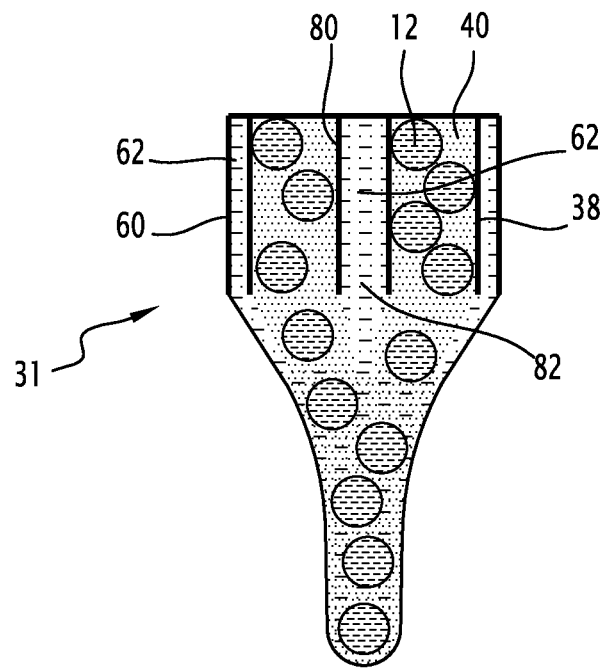
FIG. 5 is a bottom view of the end shown in FIG. 4.

In the alternative shown in FIGS. 4 and 5, the peripheral duct 60 emerges just at the outlet of the outer duct 38. The downstream edge of the peripheral duct 60 is situated at the same horizontal level as the downstream edge of the outer duct 38.

The distribution opening 66 is then situated at the same horizontal level as the downstream opening 55 of the outer circulation duct 38.

Furthermore, the stage 31 includes a central duct 80 for the injection of at least part of the solution 62 for increasing the viscosity, which extends to the center of the outer circulation duct 38.

In this example, the central duct 80 emerges just at the outlet of the outer duct 38. Its downstream edge is situated at the same horizontal level as the downstream edge of the outer duct 38.

The distribution opening 82 of the central duct 80 is therefore situated at the same horizontal level as the downstream opening 55 of the outer circulation duct 38 and the distribution opening 66 of the peripheral duct 60.

This configuration reduces the thickness of the flow comprising the drops 12, the outer fluid 40, and the solution for increasing the viscosity 62, since this flow becomes thinner by gravity upon penetrating the volume of air situated at the outlet of the duct 38, 60, 80, as illustrated by FIG. 5.

The increase of the viscosity in the outer fluid 40 is then very homogenous, since the diffusion time of the solution 62 decreases.

In an alternative illustrated by FIG. 6, the manufacturing method includes a step for increasing the capacity done in two sub-steps.

In a first sub-step 100, the quantity of base present in a first solution 62 for increasing the viscosity, injected just after the formation of the drops 12, and before their collection in the container 33, corresponds to between 1% by mass and 90% by mass, advantageously between 10% by mass and 40% by mass, of the total quantity necessary to produce the increase of the viscosity in one step.

The intermediate dispersion 102 obtained at the end of the first sub-step 100 then has a continuous phase 16 that suspends the drops 12, while remaining manipulable.

The viscosity of the continuous phase 16 in the intermediate dispersion 102 is for example less than 15,000 mPa·s, and comprised between 2500 mPa·s and 10,000 mPa·s.

The intermediate dispersion 102 can then be circulated by gravity, suction, or pressure applied on the dispersion 102.

Advantageously, the solution for increasing the viscosity 62 is injected exclusively through a central injection duct 80. Preferably, as in the configuration of FIG. 4, the central duct 80 emerges at the end of the outer circulation duct 38, such that a thinner flow forms in the volume of air and falls into the container by gravity.

The free fall and the low impact upon reception homogenize the intermediate dispersion 102.

Then, in a second sub-step 104, the intermediate dispersion 102 is recirculated in an additional duct 106, provided at its end with at least one duct 60, 80 for injecting a second solution for increasing the viscosity 62, which contains the missing quantity of base.

Preferably, the injection ducts 60, 80 are configured as in the apparatus 30 of FIG. 4, with a peripheral duct 60 and a central duct 80.

The final dispersion 10 is then recovered in the container 33.

Specific example embodiments of the method according to the invention for obtaining dispersions 10 will be described below.

EXAMPLE 1

A dispersion 10 of drops 12 of perfume, suspended in an aqueous gel, is produced using an apparatus 30 as diagrammed in FIG. 3, using the fluids described below, according to the conditions set out in Table 5.

TABLE 1

Composition of the inner fluid 36

| Name | INCI name | % by Mass |
|---|---|---|
| Lanol 99 | Isononyl Isononanoate | 0.5000 |
| Perfume | Perfume | 99.000 |
| KF 8004 | Amodimethicone | 0.5000 |
| Total | | 100.00 |

TABLE 2

Composition of the intermediate fluid 39

| Name | INCI name | % by Mass |
|---|---|---|
| Lanol 99 | Isononyl Isononanoate | 100.00 |
| Total | | 100.00 |

TABLE 3

Composition of the outer fluid 40

| Name | INCI name | % by Mass |
|---|---|---|
| Osmosed water | Water | 83.5918 |
| Glycerine codex (99%) | Glycerine | 6.2579 |
| Zemea propanediol | Propanediol | 6.2579 |
| Microcare PE | Phenoxyethanol | 1.0013 |
| Microcare emollient PTG | Pentylene Glycol | 2.5032 |
| Rhodicare T | Xanthane gum | 0.1252 |
| Tego carbomer 340 FD | Carbomer | 0.2503 |
| EDETA BD | Disodium EDTA | 0.0125 |
| Total | | 100.00 |

TABLE 4

Composition of the direct gelling solution 62

| Name | INCI name | % by Mass |
|---|---|---|
| Osmosed water | Water | 99.6622 |
| NaOH | Sodium hydroxide | 0.3378 |
| Total | | 100.00 |

TABLE 5

Flow rates used for the preparation of a perfume dispersion with direct gelling

| | % w/w | ml/h/nozzle |
|---|---|---|
| Outer fluid 36 | 10.10% | 12.10 |
| Intermediate fluid 39 | 1.12% | 1.34 |
| Outer fluid 40 | 79.90% | 90.00 |
| Solution 62 | 8.88% | 10.00 |
| Total | 100 | 113.45 |

At the end of the manufacturing method, a dispersion 10 of drops 12 of perfume is collected in the 15 g final vial, approximately 1 mm in diameter, having the composition described in Table 6.

TABLE 6 final composition of the dispersion 10 of drops 12 of perfume

| Name | INCI name | % by Mass |
|---|---|---|
| Osmosed water | Water | 75.64 |
| Lanol 99 | Isononyl Isononanoate | 1.17 |
| Perfume | Perfume | 10.00 |
| KF 8004 | Amodimethicone | 0.05 |
| Glycerine codex (99%) | Glycerine | 5.00 |
| Zemea propanediol | Propanediol | 5.00 |
| Microcare PE | Phenoxyethanol | 0.80 |
| Microcare emollient PTG | Pentylene Glycol | 2.00 |
| Rhodicare T | Xanthane gum | 0.10 |
| Tego carbomer 340 FD | Carbomer | 0.20 |
| EDETA BD | Disodium EDTA | 0.01 |
| NaOH | Sodium hydroxide | 0.03 |
| Total | | 100.00 |

EXAMPLE 2

In this example, we again use the fluids 36, 39, 40 described above in Tables 1 to 3, respectively. However, the increase of the viscosity of the continuous phase 16 is done in two sub-steps.

A preparation of intermediate dispersion 102 of 2 kg is done under the conditions described in Table 8, using a first solution 62 illustrated in Table 7 below.

TABLE 7 composition of the first pre-gelling solution 62

| Name | INCI name | % by Mass |
|---|---|---|
| Osmosed water | Water | 97.5000 |
| NaOH | Sodium hydroxide | 2.5000 |
| Total | | 100.00 |

TABLE 8

Flow rates used for the preparation of an intermediate dispersion 102 of drops 12 of perfume

| | % w/w | ml/h/nozzle |
|---|---|---|
| Inner fluid 36 | 11.05% | 12.10 |
| Intermediate fluid 39 | 1.23% | 1.34 |
| Outer fluid 40 | 87.43% | 90.00 |
| First solution 62 | 0.29% | 0.30 |
| Total | 100% | 103.75 |

The quantity of base added during this sub-step corresponds to 22.2% by mass of the desired final quantity.

The intermediate dispersion 102 is next brought into a hopper, then into the additional duct 106 so as to be able to be packaged in the final vial (15 mL).

During this sub-step, a second solution 62 containing the additional base necessary to reach the final pH and viscosity is added owing to the final gelling solution described in Table 9 below.

To obtain the correct final concentrations, the dispersion 102 and the final gelling solution 62 are placed in contact in the following weight proportions: 91.39% and 8.61%, respectively.

Thus, at the end of the conditioning method, one obtains a dispersion 10 of drops 12 of perfume of approximately 1 mm in diameter having the composition described in the Table similar to that of example 1.

TABLE 9

Composition of the final gelling solution

| Name | INCI name | % w/w |
|---|---|---|
| Osmosed water | Water | 99.7291 |
| NaOH | Sodium hydroxide | 0.2709 |
| Total | | 100.00 |

Figure 7:
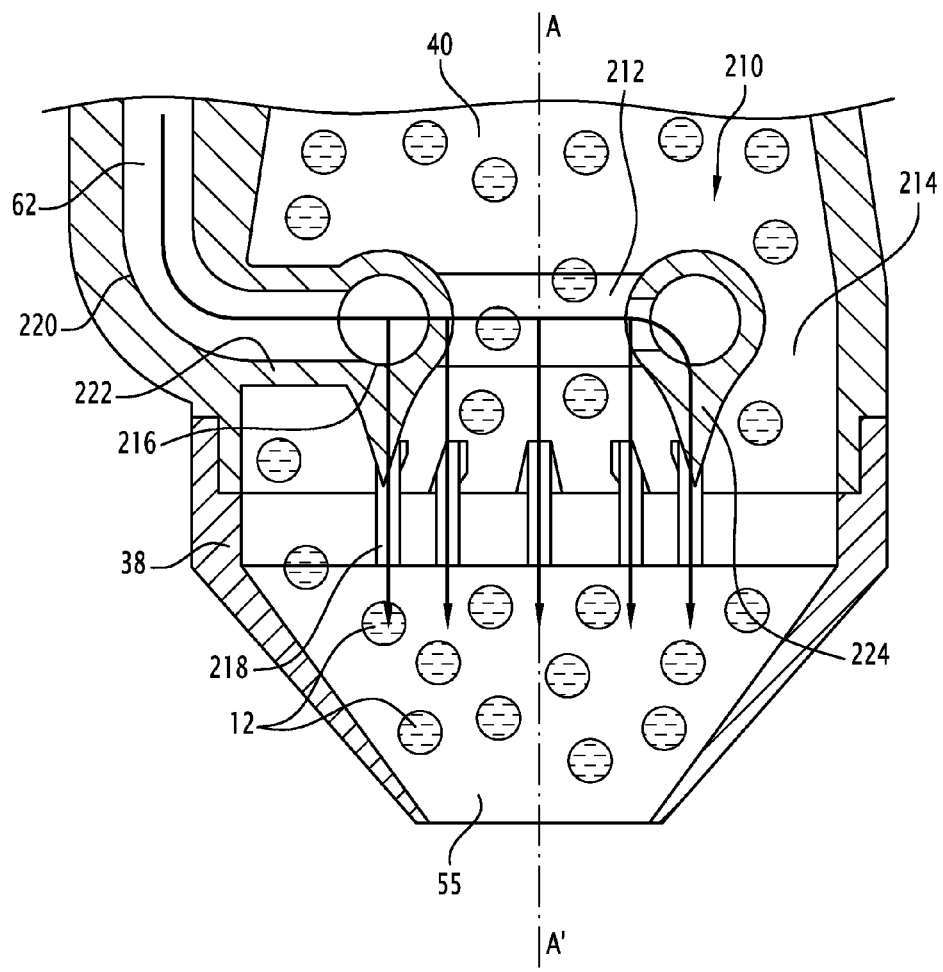
FIG. 7 is a sectional view similar to FIG. 3 of another apparatus according to the invention.

In one alternative, shown in FIG. 7, the injection duct 60 for a solution 62 for increasing the viscosity includes a downstream crown 210 for distributing the solution 62 in the outer duct 38.

The crown 210 is positioned at the center of the outer duct 38. It defines, in the outer duct 38, a central passage 212 for the circulation of drops 12, situated radially inside the downstream crown 210, and a peripheral passage 214 for the circulation of drops 12 situated radially outside the crown 210. In this example, the crown 210 is coaxial with the local axis A-A' of the duct 38. The downstream crown 210 is further positioned upstream relative to the downstream opening 55 of the outer duct 38.

The downstream crown 210 comprises a toroid 216 for distributing the solution 62, and a plurality of distribution nozzles 218, opening in the outer duct 38 downstream from the crown 210.

The toroid 216 extends over a circumference around the axis A-A'. It is connected to an upstream part 220 of the injection duct 60 by a distribution bridge 222.

In this example, the crown 210 further includes a lower wall 224 supporting the nozzles 218 that protrudes downward from the toroid 216.

Each nozzle 218 is formed by a tubular hollow body, here a needle, emerging upward in the toroid 216 and emerging downward in the outer duct 38. The nozzles 218 here extend parallel to the axis A-A'. They protrude from the lower wall 224. The nozzles 218 are distributed regularly around the axis A-A'. The number of nozzles 218 is for example comprised between 1 and 100.

During the injection of the solution 62 for increasing the viscosity, the solution passes through the upstream part 220, through the bridge 222 to reach the toroid 216. The solution is distributed in the toroid 216 around the axis A-A' and enters the nozzles 218. It is therefore injected regularly and homogenously in the duct 38, between the drops 12 circulating through the central passage 212 of the crown 210 and drops circulating through the peripheral passage 214 outside the crown 210.

The invention claimed is:

1. A method for forming a dispersion comprising drops, the method including:
    flowing drops of a first phase, through a circulation duct, into a second phase that is substantially immiscible with the first phase, each drop comprising a core formed from the first phase and a shell formed from a layer of coacervate inserted between the first phase and the second phase;
    recovering a dispersion containing drops and second phase in a container;
    injecting a solution for increasing the viscosity of the second phase in the circulation duct or at the outlet of the circulation duct, upstream from the container.

2. The method according to claim 1, wherein the drops of the second phase flow along a local axis in the circulation duct, injecting the solution increasing the viscosity being done substantially coaxially with the local axis.

3. The method according to claim 1, wherein injecting the solution increasing the viscosity includes bringing at least part of the solution increasing the viscosity to the center of the flow of the drops and the second phase.

4. The method according to claim 1, wherein injecting the solution increasing the viscosity includes bringing at least part of the solution increasing the viscosity to the periphery of the flow of the drops and the second phase.

5. The method according to claim 1, including reducing the cross-section of the flow of drops and the second phase, downstream from the injection of the solution increasing the viscosity.

6. The method according to claim 5, wherein the solution increasing the viscosity is injected at the outlet of the circulation duct.

7. The method according to claim 1, including, upstream from the flowing of the drops, forming drops in the circulation duct.

8. The method according to claim 7, wherein forming drops comprises:
    providing a first fluid comprising the first phase and a first precursor polymer of the coacervate contained in the first phase;
    forming drops of first fluid in a second fluid intended to form the second phase;
    providing a second precursor polymer of the coacervate in the second fluid.

9. The method according to claim 1, including, during the solution injection, injecting a first solution increasing the viscosity, suitable for increasing the viscosity of the second phase,
    the method comprising, after recovering the dispersion:
    returning an intermediate dispersion, comprising a second phase with a partially increased viscosity, to circulation;
    injecting a second solution increasing the viscosity into the dispersion.

10. The method according to claim 9, wherein the recirculation includes the circulation of the dispersion in an additional duct, then the recovery of the dispersion in a container at the outlet of the additional duct, the injection of the second solution increasing the viscosity being done in the additional duct, or at the outlet of the additional duct, upstream from the container.

11. The method according to claim 1, wherein the solution for increasing the viscosity contains a base.

12. The method according to claim 1, injecting the solution increasing the viscosity includes bringing at least part of the solution increasing the viscosity to the center of the circulation duct, the drops flowing in a central passage defined by the crown and in a peripheral passage defined between the crown and the circulation duct.

\* \* \* \* \*